United States Patent
Nagy

(10) Patent No.: US 12,031,978 B2
(45) Date of Patent: Jul. 9, 2024

(54) METHOD FOR DETERMINING SUSCEPTIBILITY TO SARS-CoV-2 INFECTION

(71) Applicant: Aurangzeb Nafees Nagy, Las Vegas, NV (US)

(72) Inventor: Aurangzeb Nafees Nagy, Las Vegas, NV (US)

(73) Assignee: Aurangzeb Nagy, Las Vegas, NV (US)

( * ) Notice: Subject to any disclaimer, the term of this patent is extended or adjusted under 35 U.S.C. 154(b) by 0 days.

(21) Appl. No.: 18/043,017

(22) PCT Filed: Aug. 24, 2021

(86) PCT No.: PCT/US2021/047396
§ 371 (c)(1),
(2) Date: Feb. 24, 2023

(87) PCT Pub. No.: WO2022/046803
PCT Pub. Date: Mar. 3, 2022

(65) Prior Publication Data
US 2023/0314414 A1    Oct. 5, 2023

Related U.S. Application Data

(60) Provisional application No. 63/076,479, filed on Sep. 10, 2020, provisional application No. 63/070,227, filed on Aug. 25, 2020.

(51) Int. Cl.
*G01N 33/50* (2006.01)
*G01N 33/534* (2006.01)
*G01N 33/535* (2006.01)
*G01N 33/483* (2006.01)

(52) U.S. Cl.
CPC ..... *G01N 33/5091* (2013.01); *G01N 33/5047* (2013.01); *G01N 2333/165* (2013.01); *G01N 2800/50* (2013.01)

(58) Field of Classification Search
CPC .. A61K 35/17; A61K 39/12; A61K 2039/572; A61K 39/215
See application file for complete search history.

(56) References Cited

PUBLICATIONS

Zafarani Future Virology, 2023, vol. 18, No. 3, pp. 177-191.*
Vabret et al. Immunity, vol. 52, published on Jun. 16, 2020, pp. 910-941.*
Zohar et al. Nature, vol. 20, pp. 392-394.*
Alba, Grifoni, et al.: Targets of T Cell Responses to SARS-CoV-2 Coronavirus in Humans with COVID-19 Disease and Unexposed Individuals; Cell, 2020-05-20, Elsevier, Amsterdam NL; ISSN 0092-8674; https://dx.doi.org/10.1016/j.cell.2020.05.015; vol. 181, Nr.:7, pp. 1489.
Hong-Yi, Zhen et al: Elevated exhaustion levels and reduced functional diversity of T cells in peripheral blood may predict severe progression in COVID-19 patients; Cellular & Molecular Immunology, Mar. 17, 2020, Nature Publishing Group UK, London; ISSN 1672-7681; https://dx.doi.org/10.1038/s41423-020-0401-3; vol. 17, Nr.:5, pp. 541-543.
Li, Liu, et al.: CD8+ T cells predicted the conversion of common covid-19 to severe;Nature, Scientific Reports, 11, Article No. 2169, Jan. 26, 2021; https://www.nature.com/articles/s41598-021-81732-4.pdf; https://dx.doi.org/10.1038/s41598-021-81732-4. (Annotated in IRS as "document published prior to he international filing date but later than the priority date claimed").
Sujan, Chattterjee, et al.: Various theranostics and immunization strategies based on nanotechnology against Covid-19 pandemic: An interdisciplinary view; Life Science, May 12, 2021, Pergamon Press, Oxford, GB; ISSN 0024-3205; https://dx.doi.org/10.1016/j.lfs.2021.119580; vol. 278. (Annotated in IRS as "document published prior to he international filing date but later than the priority date claimed").
Vabret, Nicholas, et al.: Immunology of COVID-19: Current State of the Science; Immunity, May 6, 2020, Cell Press, Amsterdam, NL; ISSN 1074-7613; https://dx.doi.org/10.1016/j.immuni.2020.05.002; vol. 52, Nr.:6, pp. 910-941.
Younggang, Zhou, et al.: Aberrant pathogenic GM-CSF+ T cells and inflammatory CD14+ CD16+ monocytes in severe pulmonary syndrome patients of a new coronavirus; bioRxiv, Feb. 20, 2020; https://www.biorxiv.org/content/10.1101/2020.02.12.945576v1.full.pdf; https://dx.doi.org/10.1101/2020.02.12.945576.
Zehu, Chen et al.: T cell responses in patients with COVID-19; Nature reviews Immunology, vol. 20, Sep. 1, 2020; https://www.nature.com/articles/s41577-020-0402-6.pdf; pp. 529-536.
International Search Report dated Nov. 15, 2021 for International Application No. PCTUS2021047396 filed on Aug. 24, 2021.

* cited by examiner

*Primary Examiner* — Bao Q Li
(74) *Attorney, Agent, or Firm* — Connie R. Masters

(57) ABSTRACT

A method for determining a susceptibility of a patient to infection by SARS-CoV-2 virus includes obtaining a tissue sample from the patient. The method also includes obtaining first cells from the tissue sample. The method further includes adding the first cells to second cells infected with the SARS-CoV-2 virus. Moreover, the method includes measuring a property of the second cells related to death of the second cells after adding the first cells to the second cells. In addition, the method includes calculating a susceptibility of the patient to infection by the SARS-CoV-2 virus using at least the property of the second cells.

20 Claims, 7 Drawing Sheets

200

202 — Incubate SARS-CoV-2 infected target cells with $^{51}$Cr

204 — Wash target cells to remove $^{51}$Cr

206 — Add serially diluted patient PBMN cells to aliquots of incubated target cells 208 — Set up negative and positive controls 210 — Measure amounts of $^{51}$Cr released into supernatant by target cells, and negative and positive controls 212 — Calculate % cytotoxicity using the measured amounts

FIG. 2

METHOD FOR DETERMINING SUSCEPTIBILITY TO SARS-CoV-2 INFECTION

FIELD OF THE INVENTION

The present invention relates generally to processes for determining patient susceptibility to infection by the SARS-CoV-2 virus.

BACKGROUND

Coronavirus Disease 2019 ("COVID-19") is a pandemic severely impacting the health and lives of the entire human population on the planet. From an estimated first infection in the fall of 2019 to August 2020, more than 21 million cases of COVID-19 have been confirmed worldwide, and more than 750,000 deaths attributable to COVID-19 have been recorded. Severe Acute Respiratory Syndrome Coronavirus 2 ("SARS-CoV-2") is a member of the Coronaviridae family, genus *Betacoronavirus*, which causes COVID-19. SARS-CoV-2 has estimated basic reproductive number ("$R_0$") of between 1.4 and 5.7 secondary infections per infected index case, making it highly contagious and rapidly spreading virus.

There are six other coronaviruses that are known to infect humans. Four of these cause the common cold, and the other two cause potentially lethal diseases. These other two coronaviruses are severe acute respiratory syndrome coronavirus ("SARS-CoV") and Middle East respiratory syndrome coronavirus ("MERS-CoV"). These two viruses are believed to have originated in animal populations.

SARS-CoV-2 is a positive-sense, single-stranded RNA virus with linear RNA that is currently believed to primarily spread from infected human patients via respiratory droplets. The virus size is about 60 to 200 nanometers. The full genome of SARS-CoV-2 is about 30,000 bases in length and has been sequenced from RNA extracted from patient samples. SARS-CoV-2 includes four structural proteins: spike or S protein; envelope or E protein; membrane or M protein; and nucleocapsid or N protein. The spike, E, and M proteins enclose the viral genetic core, which includes the linear RNA. The RNA is tightly packed within the core by the N proteins. The spike protein is the portion of the virus that is thought to interact with cell membrane surface proteins in target cells to allow the virus to enter those cells. The spike protein is disposed on the surface/envelope of the virus.

On day zero of infection with the SARS-CoV-2 virus, the virus infects the epithelium of the nasal sinuses, travels down to the lungs, and by day two, the viral load in the lungs is similar to that in the nasal passages. By day four, the infectious process of the lungs is well underway with typical symptoms of viral lower respiratory infection (dry cough, sore throat, shortness of breath, fever, etc.). By day seven, the viral activity has mostly been suppressed by patients with a normally functioning immune system, although the viral RNA continues to be detectable as far as 21 days from onset of symptoms. This suggests that patients are still contagious as far as 21 days from onset of symptoms. Although initial viral load likely influences the ability of the body to fight the infection, clinical data indicate that once symptoms develop, serum virus concentration is unrelated to patient outcome. Age correlates positively with poor outcome, likely due to immune-senescence normally found in the aged.

SARS-CoV-2 seems to affect some people more severely than others. While most infected patients have mild symptoms, others have high morbidity and may die. Much speculation exists as to why this occurs. Experts surmise that 50% of the reason is genetic. Patients with type-A blood or with certain HLA types are more susceptible; however these observations do not adequately explain the difference.

The COVID-19 disease process branches into three pathways at day seven. A large percentage of patients will begin to recover. A second population of patients may develop cytokine storm. A third population of patients does not recover from the disseminated viral infection, develops diffuse organ failure, and succumbs.

In the cytokine storm pathway, cytotoxic immune cells (e.g. cytotoxic T lymphocytes and natural killer cells) attack target cells infected with the SARS-CoV-2 virus, which are presenting viral proteins on their surfaces. Normally, the cytotoxic immune cells will produce a protein called perforin that penetrates the target cell membrane. The cytotoxic immune cells will then release multiple cytotoxic agents into the perforated target cell, which cause apoptosis. Simultaneously, the cytotoxic immune cells secrete other cytokines (e.g., transforming growth factor beta (TGF-ß), Interleukin 6 (IL-6)) that summon macrophages to the site in order to clean up the debris formed during apoptosis.

In 10-15% of the population, one of the two copies of the perforin gene is defective, making these patients susceptible to perforin malfunction. In the right circumstances, these patients will experience impairment in the ability of the cytotoxic immune cells to utilize perforin to kill the target cell infected with the virus. However, the cytotoxic immune cells will continue to secrete cytokines to summon macrophages to the area. The macrophages that are summoned to the area, although initially summoned for cleanup, also release their own cytokines. In the resulting cytokine storm, the macrophages increase the deposition of fibrin. This macrophage secreted fibrin, along with extracellular matrix secreted by fibroblasts, leads to areas of pulmonary fibrosis/restriction in COVID-19, and the ground-glass appearance seen on chest X-rays. A build-up of TGF-ß causes the epithelial cells lining the lungs to convert into connective tissue fibroblasts. The combination of excess fibrin and fibroblasts may increase inappropriate blood clotting, which has been seen frequently in COVID-19. Accordingly, patients with COVID-19 may have an increased disposition to develop stroke and inappropriate blood clotting in the small vessels of the extremities.

The virus infects many cells rapidly starting in the nasal passages and then the lungs. The virus progresses rapidly because the molecular target for the virus that allows entry into cells is so widely expressed on so many cells and cell types. In most individuals, the body's natural immune system is able to clear the virus. In a few individuals, the body fails to clear the virus and a cytokine storm develops, which often goes on to kill the patient. Currently the cytokine storm is treated with dexamethasone and interleukin-6 ("IL-6") antagonists while the virus itself is treated with remdesivir.

Cytokine storm occurs when cytotoxic CD8+ T cell or natural killer cell lines attach to a virus-infected cell and the virus-infected cell fails to die. Specifically, after NK cells and CD8+ cells bind to a cell infected with the SARS-CoV-2 virus, they release a molecule called perforin that makes a perforation in the target cell and other toxins from the CD8+ or NK cells enter the target cell causing the cell to undergo apoptosis and die. During this process, the NK and CD8+ cells secrete cytokines until the target cell undergoes apoptosis and then they stop secreting pro-inflammatory cytokines and switch to producing anti-inflammatory cytokines. In some patients the perforin does not function properly (5 to 15% of the population carries defective perforin genes). The target cell then never undergoes apoptosis, so the NK cell and the CD8+ cells keep producing pro-inflammatory cytokines, causing the cytokine storm.

The SARS-CoV-2 virus passes into the bloodstream in the area of the alveolar capillaries due to direct attack on the vessels by the virus, oxidative damage to endothelial cells caused by released exotoxin vesicles from white blood cells, and due to the increased permeability of the blood vessels caused by the inflammatory response. The virus then disseminates through the blood to the intestinal mucosa, kidneys, and spleen with demonstrable presence of virus and damage in those areas by day four after infection.

One theory of infection is that the SARS-CoV-2 spike protein binds to type 2 angiotensin-converting enzyme ("ACE2") receptors on target human cells to facilitate SARS-CoV-2 entry into those cells. ACE2 receptors are present in most cells in the human body, but it is highly expressed on cilia-containing cell membranes, including those of lung alveolar type II cells, epithelial cells of the gastrointestinal system, and renal tubule epithelium in the kidney. ACE2 receptor normally cleaves angiotensin two creating smaller protein fragments that have anti-inflammatory properties. When large numbers of SARS-CoV-2 virus are present, much of the ACE2 receptor is bound, reducing cleavage of angiotensin two, which builds up. According to some theories, the loss of the anti-inflammatory protein fragment cleavage products contributes to the aggressive inflammatory response cause by the SARS-CoV-2 virus. According to other theories, other effects of the buildup of angiotensin two include cardiomyopathy (SARS-CoV-2 virus binding to cardiocyte ACE2 receptors) and stroke (SARS-CoV-2 virus binding to cerebrovascular endothelial cells ACE2 receptors).

After the SARS-CoV-2 virus binds to the human ACE2 receptor, surface proteases such as transmembrane serine protease 2 ("TMPRSS2") facilitate proteolytic activation, fusion, and internalization of the SARS-CoV-2 virus into endosomes in the target cell. After the SARS-CoV-2 virus has been internalized into target cell endosomes, lysosomal cathepsin ("CTSL") proteins release the SARS-CoV-2 virus into the cytoplasm of the target cell to further the infection. The binding, internalization, and release of the SARS-CoV-2 virus in the target cell thereby facilitate SARS-CoV-2 infection of the target cells.

The list of reported symptoms of COVID-19 from sources such as the United States Centers for Disease Control and Prevention ("CDC") is growing and evolving. A large number of varied symptoms have been reported from different groups of patients worldwide. COVID-19 symptoms can range from mild to severe disease. COVID-19 symptoms generally appear between 2 to 14 days after exposure to SARS-CoV-2 virus particles. Common symptoms of COVID-19 include cough, shortness of the breath, fever, and fatigue. Other symptoms such as headache, chills, muscle or joint aches, and sore throat can be seen in a number of patients. Impairment of taste and smell has also been reported. Liver enzyme abnormalities and a tendency to form blood clots may occur during infection.

Patients with severe or critical disease often show evidence of a cytokine release syndrome (cytokine storm) with manifestations of progressive pneumonia, respiratory failure, kidney failure, or hypotension, frequently resulting in death. The evidence of cytokine storms in severely or critically ill patients includes high levels of cytokines (e.g., interleukin-6) in the blood of such patients. As described herein, during a cytokine storm, a patient's body begins to attack their own cells and tissues in addition to fighting infection.

According to some theories, cytokine storm in certain patients infected with the SARS-CoV-2 virus results from the virus' ability to quickly replicate in infected cells. These cells respond by releasing large amounts of cytokines to kill themselves to prevent spread of the disease. Unfortunately, the cytokine storm resulting from the large amounts of cytokine proteins also kills neighboring cells. In SARS-CoV-2 virus infections, much of the cell death occurs in lung tissue, resulting in damage to the gas transferring surfaces of the lungs, which can be exacerbated by becoming filled with fluids (i.e., "waterlogged"). Diffuse alveolar damage can result from cell death in lung tissue and can include the deposition of hyaline membranes made up of dead cells, proteins, and surfactant. Hyaline membrane deposition can limit gas exchange in the lungs and cause the lung tissue to become waterlogged. This lung damage can result in pneumonia with the patient dying from an inability to manage gas exchange (e.g., lack of oxygen, too much carbon dioxide).

Early response to infection by the SARS-CoV-2 virus (e.g., by natural killer cells ("NK cells")) can be an indicator of susceptibility of a patient to infection by the SARS-CoV-2 virus, and the degree of morbidity associated with such infections in that patient. NK cells are a class of white blood cells that have a substantial role in battling viral infections by killing host cells infected with viruses. NK cells have cytoplasmic granules that contain granzymes (e.g., perforin and proteases), which can kill cells in their proximity. NK cells are drawn to virally infected cells (e.g., by interferons and cytokines released) in response to the viral infections.

Once in proximity to virally infected cells, NK cells release granzymes from their cytoplasmic granules. Degranulation is associated with expression of CD107a ("lysosomal-associated membrane protein 1" or "LAMP1"), which is a sensitive marker of NK cell activity. Perforin creates openings in the cell membranes of the virally infected cells. Other granzymes enter the virally infected cells via these openings and kill the virally infected cells ("apoptosis"). Apoptosis kills both the virally infected cells and viruses, compared to simple lysis, which would release the viruses in virally infected cells. As such, NK cells limit viral infections by causing apoptosis in the general vicinity of virally infected cells while more specific adaptive immune response builds (e.g., virus specific cytotoxic T cells). Consequently, failures of NK cell response can render a patient susceptible to early stages of viral infections because the virus can then replicate fast enough to spread rapidly and overwhelm the body before the adaptive immune response can suppress it.

COVID-19 is caused by the SARS-CoV-2 virus, which belongs to a sizable family of coronaviruses. Multiple strains of SARS-CoV-2 have been identified, but conserved sequences allow for the use of molecular diagnostic tools. Polymerase chain reaction ("PCR") using primers from the SARS-CoV-2 genome (e.g., N protein and Open Reading Frame 1b (ORF1b)) primers as produced amplified overlapping fragments covering substantially the entire viral genome.

Leveraging low variability of the SARS-CoV-2 genomic RNA sequence, several PCR/nucleic acid tests were developed to detect the SARS-CoV-2 virus early in the course of the COVID-19 pandemic. Later in the COVID-19 pandemic, many academic and commercial laboratories refined and improved these PCR/nucleic acid tests, which continued to vary in sensitivity (high sensitivity=high true positive rate/low false negative rate) and specificity (high specificity=high true negative rate/low false positive rate).

Many of these PCR/nucleic acid base tests utilize the oropharyngeal and/or nasopharyngeal swab sample collection method recommended by the CDC, which retrieves samples from the respiratory mucosa at the rear of the nasal passage and throat (i.e., the nasopharynx). These may be placed in viral transport medium. Samples used for testing in clinical practice also include mid-turbinate samples, nasal washes, and nasal swabs (which are easier to obtain than nasopharyngeal swabs), sputum, bronchoalveolar lavage fluid, and saliva samples.

Antibody-based tests have also been developed to detect antibodies against SARS-CoV-2 virus specific proteins in the blood of patients, again with varying degrees of sensitivity and specificity. However, both PCR/nucleic acid ("molecular") and antibody-based ("serological") tests have various limitations. These limitations relate to sensitivity, specificity, and timing of these tests. For instance, no current test will identify an infected patient before the first 5 to 7 days after exposure to the SARS-CoV-2 virus. Even after the onset of symptoms, IgM and IgG may not be detectable for about five days. Viral loads drop below detectable levels about 25 days after exposure. While some antibodies remain after 25 days after exposure, declining levels of antibodies can affect the sensitivity of tests.

While diagnostic assays (with limitations) are being developed for infection by the SARS-CoV-2 virus, there is no current test for a patient's susceptibility to infection by the SARS-CoV-2 virus (i.e., the morbidity expected for a particular patient following exposure to the SARS-CoV-2 virus). A test for a patient's susceptibility to infection can provide many options for management of the worldwide COVID-19 infection. For instance, segments of the population who have low susceptibility to infection by the SARS-CoV-2 virus and/or indications of low morbidity associated with such infections can move more freely in the population while taking reasonable precautions. Such low susceptibility individuals can return to the workforce to control the economic costs of COVID-19 pandemic mitigation (e.g., from shelter in place orders and travel restrictions).

Accordingly, there is a need for methods for determining patient susceptibility to infection by the SARS-CoV-2 virus. Ideally, such tests would be highly sensitive and specific. If a test could determine the ability of a patient's CD8+ cells and/or NK cells to kill target cells infected with the SARS-CoV-2 virus, the resulting data could be used to determine whether that patient is susceptible to COVID-19.

SUMMARY

Embodiments are directed to methods for determining patient susceptibility to infection by the SARS-CoV-2 virus. In particular, the embodiments are directed to methods for determining patient susceptibility to infection by the SARS-CoV-2 virus using standard tissue sample collection techniques. The resulting tests would have relatively high sensitivities and specificities.

In one embodiment, a method for determining a susceptibility of a patient to infection by SARS-CoV-2 virus includes obtaining a tissue sample from the patient. The method also includes obtaining first cells from the tissue sample. The method further includes adding the first cells to second cells infected with the SARS-CoV-2 virus. Moreover, the method includes measuring a property of the second cells related to death of the second cells after adding the first cells to the second cells. In addition, the method includes calculating a susceptibility of the patient to infection by the SARS-CoV-2 virus using at least the property of the second cells.

In one or more embodiments, the tissue sample is blood from the patient. The first cells may be peripheral blood mononuclear cells of the patient. The first cells may be NK cells of the patient. The method may include obtaining the first cells using fluorescent-activated cell sorting, magnetic-activated cell sorting, or flow cytometry. The method may include obtaining the first cells by removing other cells from the tissue sample using leukapheresis.

In one or more embodiments, the second cells are cells of the patient. The method may include infecting the cells of the patient with the SARS-CoV-2 virus before adding the first cells to second cells. The second cells may be epithelial cells from the patient. The second cells may be mucosal cells from the patient. The second cells may be nasal cells from the patient. The second cells may be cells of a cell line not related to the patient.

In one or more embodiments, the property of the second cells is a level of radioactivity in the second cells. The method may include measuring the level of radioactivity in the second cells using a gamma counter or a scintillation counter. The property of the second cells may be a level of fluorescence in the second cells. The method may include measuring the level of fluorescence in the second cells using a spectrophotometer.

In one or more embodiments, the method includes calculating a susceptibility index for the patient using at least the property of the second cells. The susceptibility index may be a numerical index. The susceptibility index may be a lytic unit.

In one or more embodiments, the method includes growing the second cells in a first solution including a factor related to the property before adding the first cells to the second cells. The factor may be a radio-labeled marker or a fluorescent marker. The method may include preparing a negative control by incubating a first aliquot of second cells infected with the SARS-CoV-2 virus in media, and preparing a positive control by incubating a second aliquot of second cells in a lysis buffer. The method may include washing the second cells to remove the first solution including the factor from the second cells before adding the first cells in a second solution to the second cells.

In one or more embodiments, adding the first cells in the second solution to second cells infected with the SARS-CoV-2 virus includes diluting the first cells to generate a plurality of aliquots of first cells having different concentrations, and adding the plurality of aliquots of first cells to a respective plurality of second cells infected with the SARS-CoV-2 virus. The method may include incubating the plurality of aliquots of first cells and the respective plurality of second cells in respective aliquots of the second solution. The method may include measuring the factor in the each of the respective aliquots of the second solution after incubating respective pairs of the plurality of aliquots of first cells and the plurality of second cells therein to obtain a plurality of measured values of the factor corresponding to the plurality of aliquots of first cells having different concentrations. The method may include calculating the susceptibility of the patient to infection by the SARS-CoV-2 virus by calculating a plurality of percent cytotoxicity values corresponding to the plurality of aliquots of first cells having different concentrations using the plurality of measured values of the factor, and generating a cytotoxicity dose response curve based on the plurality of percent cytotoxicity values.

In one or more embodiments, the method includes calculating a lytic unit value by analyzing the cytotoxicity dose response curve using linear regression, exponential fit, or a Von Krogh mathematical model. The method may include calculating a lytic unit value based on a dilution ratio at 10% cytotoxicity on the cytotoxicity dose response curve. The method may include calculating the susceptibility of the patient to infection by the SARS-CoV-2 virus by comparing the lytic unit value of the patient to a plurality of known lytic unit values of a plurality of patients having known susceptibilities to infection by the SARS-CoV-2 virus.

In one or more embodiments, the method is performed at least partially using a microfluidic device or a biochip. After obtaining the tissue sample from the patient, the method may be performed without further human intervention.

In another embodiment, a method for determining a susceptibility of a patient to infection by SARS-CoV-2 virus includes obtaining a tissue sample from the patient. The method also includes obtaining first cells from the tissue sample. The method further includes adding the first cells to second cells infected with the SARS-CoV-2 virus. Moreover, the method includes measuring a property of the first cells after adding the first cells to the second cells. In addition, the method includes calculating a susceptibility of the patient to infection by the SARS-CoV-2 virus using at least the property of the first cells.

In one or more embodiments, the method includes adding an antibody directed to an antigen related to the property of the first cells to the second cells infected with the SARS-CoV-2 virus along with the first cell, and incubating the antibody, the first cells, and the second cells before measuring the property of the first cells. The method may include preparing a negative control by incubating a first aliquot of first cells with the antibody in media, and preparing a positive control by incubating a second aliquot of first cells with a superantigen and the antibody in media.

In one or more embodiments, the method includes washing the first cells to remove the antibody before measuring the property of the first cells. The method may include incubating the first cells with an antibody directed to an antigen specific to a cell type. The method may include measuring the property of the first cells of the cell type. The cell type may be NK cells. The antigen may be CD107a, and the property of the first cells is a level of surface CD107a expression. The method may include measuring the property of the first cells using flow cytometry.

In still another embodiment, a method for determining a susceptibility of a patient to infection by SARS-CoV-2 virus includes obtaining a tissue sample from the patient. The method also includes obtaining first cells from the tissue sample. The method further includes adding the first cells to second cells infected with the SARS-CoV-2 virus in a first media. Moreover, the method includes measuring a property of the first medium after adding the first cells to the second cells. In addition, the method includes calculating a susceptibility of the patient to infection by the SARS-CoV-2 virus using at least the property of the first medium.

In one or more embodiments, the method includes adding an antibody directed to an antigen released by the first cells to the first medium, and incubating the antibody, the first cells, and the second cells in the first medium before measuring the property of the first medium. The method may include preparing a negative control by incubating a first aliquot of first cells with the antibody in a second media, and preparing a positive control by incubating a second aliquot of first cells with a superantigen and the antibody in a third media.

In one or more embodiments, the method includes removing unbound antibody from the first media before measuring the property of the first media. The unbound antibody may be removed from the first media using photo-spectrometry, mass-spectrometry, or electrophoresis. The property of the first media may be an amount of a complex of the antibody and the antigen therein. The antigen may be perforin.

In still another embodiment, a method for determining a susceptibility of a patient to infection by SARS-CoV-2 virus includes obtaining peripheral blood mononuclear cells from the patient. The method also includes measuring an amount of T cells specific to a SARS-CoV-2 related protein in the peripheral blood mononuclear cells. The method further includes calculating a susceptibility of the patient to infection by the SARS-CoV-2 virus using at least the measured amount of T cells in the peripheral blood mononuclear cells.

In one or more embodiments, the SARS-CoV-2 related protein is SARS-CoV-2 spike protein, M protein, or N protein, and the T cells are CD4+ or CD8+. The method may include measuring the amount of T cells specific to the SARS-CoV-2 related protein in the peripheral blood mononuclear cells using flow cytometry. The patient may not have been exposed to the SARS-CoV-2 virus.

In yet another embodiment, a method for determining a susceptibility of a patient to infection by SARS-CoV-2 virus includes obtaining peripheral blood mononuclear cells from the patient. The method also includes measuring an amount of T helper cells specific to a SARS-CoV-2 related protein in the peripheral blood mononuclear cells. The method further includes calculating a susceptibility of the patient to infection by the SARS-CoV-2 virus using at least the measured amount of T cells in the peripheral blood mononuclear cells.

In one or more embodiments, the SARS-CoV-2 related protein is SARS-CoV-2 spike protein, M protein, or N protein. The method may include measuring the amount of T helper cells specific to the SARS-CoV-2 related protein in the peripheral blood mononuclear cells using flow cytometry. The patient may not have been exposed to the SARS-CoV-2 virus.

In yet another embodiment, a method for determining a susceptibility of a patient to infection by SARS-CoV-2 virus includes obtaining a tissue sample from the patient. The method also includes obtaining first cells from the tissue sample. The method further includes labeling second cells infected with the SARS-CoV-2 virus. Moreover, the method includes adding the first cells to the labeled second cells infected with the SARS-CoV-2 virus. In addition, the method includes acquiring images of the labeled second cells infected with the SARS-CoV-2 virus while incubating with the first cells. The method also includes analyzing the acquired images to determine a number of the labeled second cells infected with the SARS-CoV-2 virus. The method further includes calculating a susceptibility of the patient to infection by the SARS-CoV-2 virus using at least the number of the labeled second cells infected with the SARS-CoV-2 virus.

In one or more embodiments, the tissue sample is blood, and the first cells are NK cells. The second cells infected with the SARS-CoV-2 virus may be labeled with a fluorescent dye. The method may include washing the labeled second cells infected with the SARS-CoV-2 virus before adding the first cells to the labeled second cells infected with the SARS-CoV-2 virus.

In one or more embodiments, adding the first cells to the labeled second cells infected with the SARS-CoV-2 virus includes diluting the first cells to generate a plurality of aliquots of first cells having different concentrations, and adding the plurality of aliquots of first cells to a respective plurality of second cells infected with the SARS-CoV-2 virus. The method may also include generating a plurality of negative controls by diluting unlabeled second cells to generate a plurality of aliquots of unlabeled second cells having different concentrations, and adding the plurality of aliquots of unlabeled second cells to a respective plurality of second cells infected with the SARS-CoV-2 virus.

The aforementioned and other embodiments of the invention are described in the Detailed Description which follows.

BRIEF DESCRIPTION OF THE DRAWINGS

The foregoing and other aspects of embodiments are described in further detail with reference to the accompanying drawings, in which the same elements in different figures are referred to by common reference numerals, wherein:

FIGS. 1 and 2 are flowcharts depicting methods for determining patient susceptibility to infection by the SARS-CoV-2 virus using an NK cell cytotoxicity assay according to some embodiments.

Figure 1:
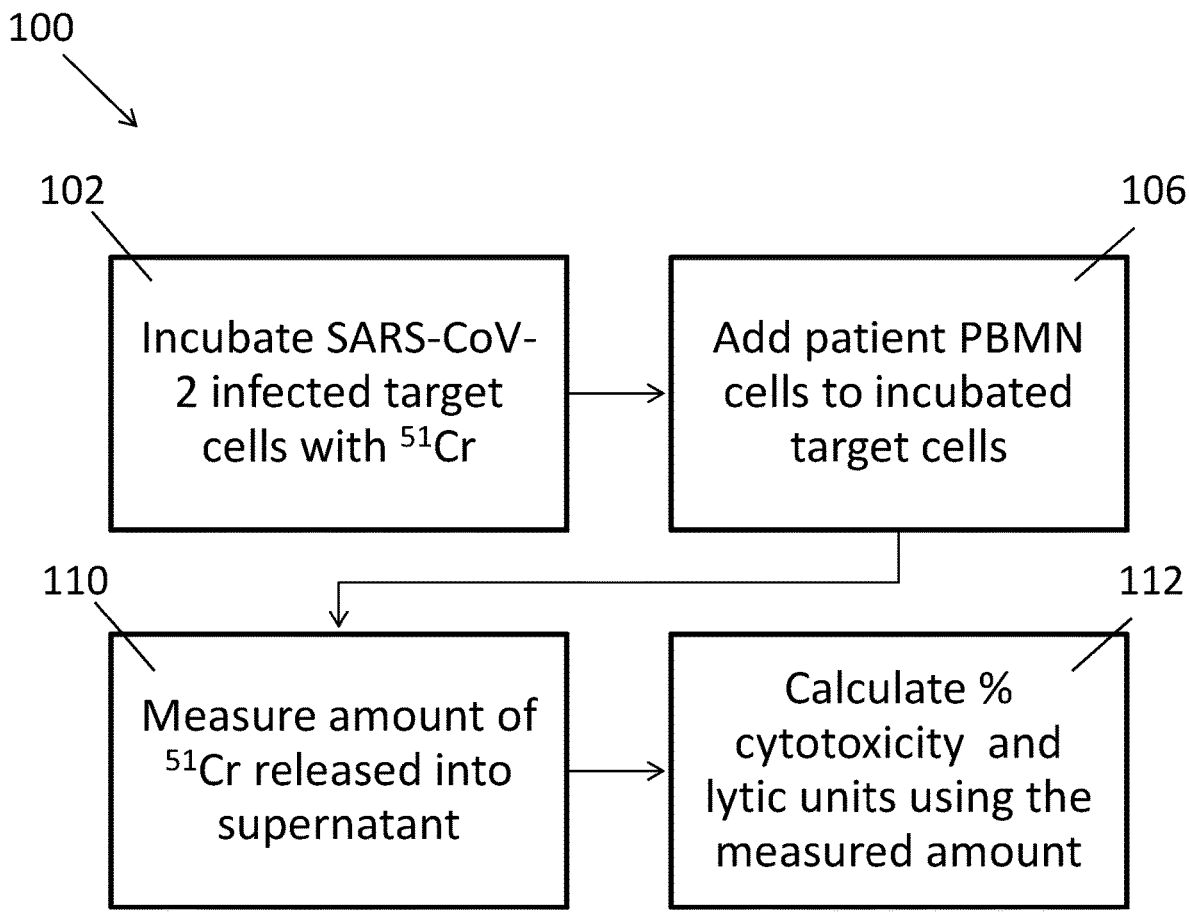

In order to better appreciate how to obtain the above-recited and other advantages and objects of various embodiments, a more detailed description of embodiments is provided with reference to the accompanying drawings. It should be noted that the drawings are not drawn to scale and that elements of similar structures or functions are represented by like reference numerals throughout. It will be understood that these drawings depict only certain illustrated embodiments and are not therefore to be considered limiting of scope of embodiments.

DETAILED DESCRIPTION OF ILLUSTRATED EMBODIMENTS

In some embodiments, testing for a patient's susceptibility to infection by the SARS-CoV-2 virus includes using an NK cell cytotoxicity assay. As described above, NK cells are drawn to virally infected cells and release granzymes in their vicinity to cause apoptosis of the virally infected cells. Therefore, NK cells can determine a patient's susceptibility to early stages of viral infections.

Exemplary Method for Determining Susceptibility to SARS-CoV-2 Using NK Cytotoxicity Assay Determining the ability of a patient's NK cells to cause apoptosis of cells infected with SARS-CoV-2 can indicate that patient's susceptibility to infection by SARS-CoV-2. FIGS. 1 and 2 are flowcharts depicting two similar methods 100, 200 for determining patient susceptibility to infection by the SARS-CoV-2 virus using an NK cell cytotoxicity assay according to some embodiments.

At steps 102 and 202, target cells infected with the SARS-CoV-2 virus are incubated with chromium-51. A variety of human cells are susceptible to infection by the SARS-CoV-2 virus. Susceptibility to infection may correlate to the presence/high expression of ACE2 receptors and various proteases (e.g., TMPRSS2 and CTSL) in various human cells. Human cells with high levels of ACE2 receptor and TMPRSS2 and/or cathepsin protease expression include but are not limited to various cell types in the human lungs, nose, heart, liver, kidney, pancreas, bladder, prostate, testes, Ileum, eyes, and brain. Accordingly, any of these cells would be suitable target cells for the instant method. In particular, nasal cells (e.g., ciliated, basil, and goblet cells) express both relatively high levels of the ACE2 receptor and the TMPRSS2 protease, making it both a suitable and relatively accessible target cell. In some embodiments, the target cells may be the patient's own nasal cells, which are collected (e.g., via a nasopharyngeal swab) and cultured. In other embodiments, the target cells may be an existing line of human nasal cells that are not from the patient. In any case, the nasal cells may be infected with the SARS-CoV-2 virus by exposure thereto and incubation in an appropriate medium.

As described above, at steps 102 and 202, the SARS-CoV-2 infected target (e.g., human nasal) cells are incubated in media containing the radioisotope chromium-51, which will be incorporated into the target cells during incubation. In other embodiments, the media can include a fluorescent marker, which will be incorporated into the target cells during incubation. While the methods 100, 200 described herein utilize chromium-51 as a radioactive marker for apoptosis, in other embodiments, other radioactive markers (e.g., nitrogen-15, phosphorous-32, and sulfur-35) can be used. Adding these radioactive markers to media (e.g., agar culture media) will lead to uptake of the radioactive markers by the target cells.

At step 204, the incubated target cells are washed to remove the chromium-51 that has not incorporated into the target cells.

At steps 106 and 206, peripheral blood mononuclear ("PBMN") cells are collected from the patient (e.g., using density gradient centrifugation) and incubated with the target cells. Blood can be collected from the patient and PBMN cells can be isolated as described above. PBMN cells include various cells involved in the immune response, including but not limited to NK cells. PBMN cells collected from the patient are incubated with the target cells after the media containing chromium-51 is replaced with normal media. During incubation, NK cells in the PBMN cells will cause apoptosis of target cells infected with SARS-CoV-2.

At step 206, the PBMN cells are serially diluted at ("effector: target") ratios of 50:1, 25:1, 12.5:1, and 6.25:1. Each of these serially diluted amounts of PBMN cells are incubated with target cells.

At step 208, negative and positive controls are generated. A negative control is generated by incubating the target cells with only media. A positive control is generated by incubating the target cells with a substance (e.g., a lysis buffer) that will lyse substantially all of the target cells.

Figure 3:
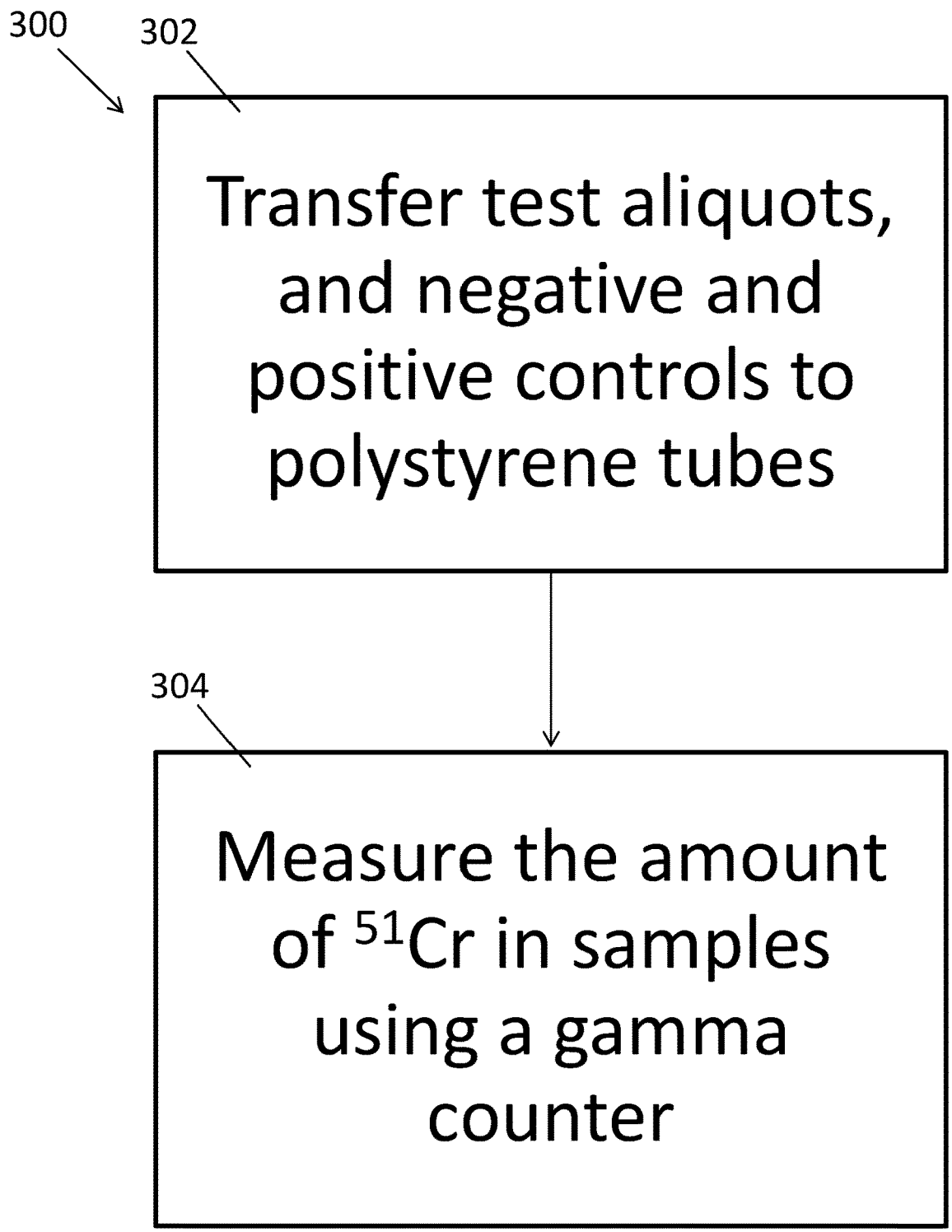
FIG. 3 is a flowchart depicting a method for measuring the amount of chromium-51 in a sample using a gamma counter according to some embodiments.
Figure 4:
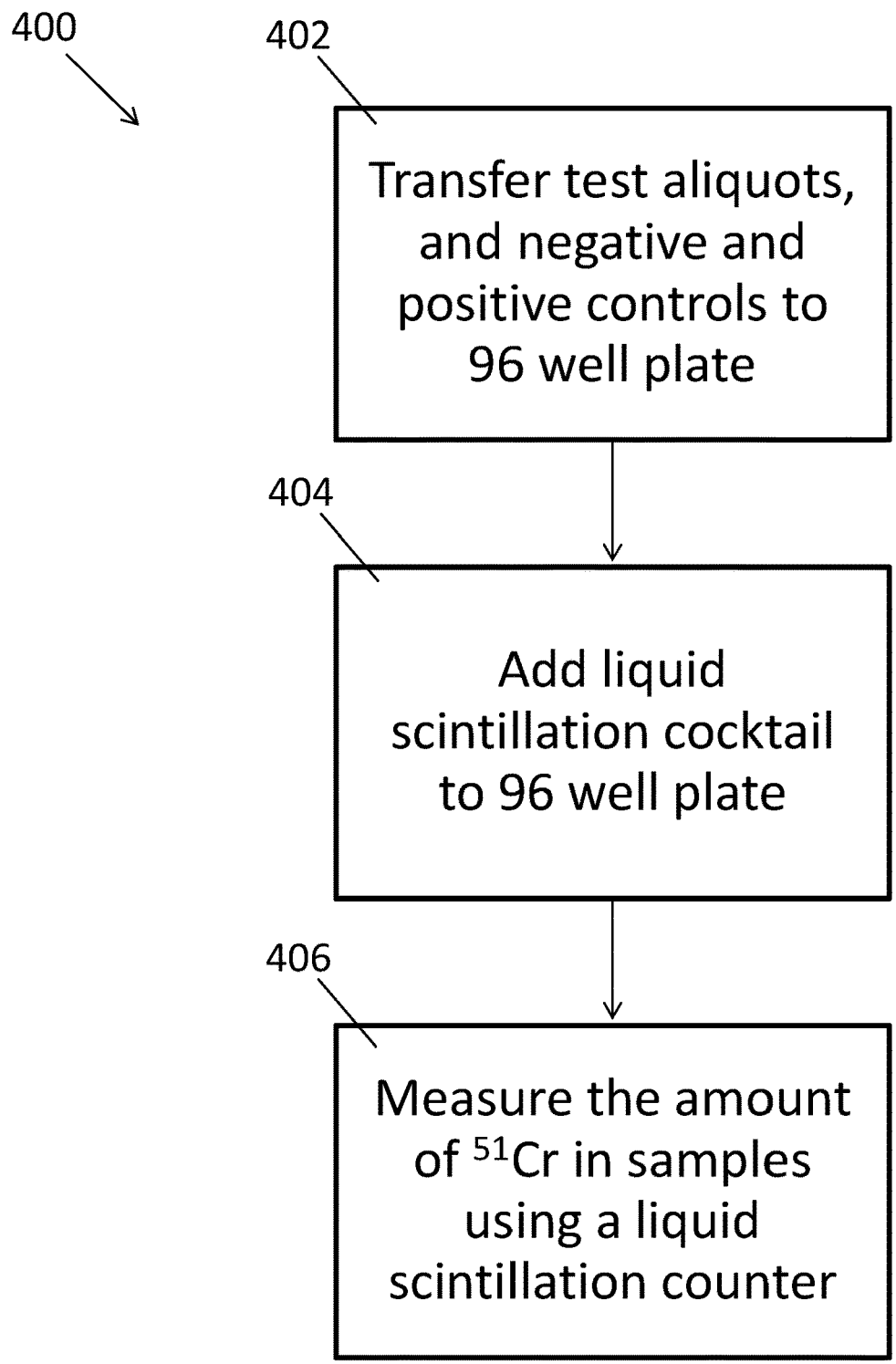
FIG. 4 is a flowchart depicting a method for measuring the amount of chromium-51 in a sample using a scintillation counter according to some embodiments.

At steps 110 and 210, the incubated PBMN cells and target cells are pelleted by centrifugation and the supernatant is collected. When NK cells cause apoptosis of the target cells during incubation, chromium-51 (or other radioactive markers) is released into the supernatant. Then the amount of chromium-51 in the supernatant is measured. The amount of chromium-51 can be measured using a gamma counter as shown in FIG. 3. Alternatively, the amount of chromium-51 can be measured using a scintillation counter after adding scintillation fluid to the supernatant as shown in FIG. 4. In other embodiment, the amount of fluorescent marker can be measured using a spectrophotometer.

At step 210, amount of chromium-51 in the serially diluted PBMN cells, the negative control, and the positive control are measured.

At steps 112 and 212, the percent cytotoxicity and lytic unit are calculated using the measured amount of chromium-51 in the supernatant as described herein.

At step 212, the percent cytotoxicity for each serially diluted amount of PBMN cells is calculated using the following formula.

$$\% \text{ cytotoxicity} = 100 * \frac{\text{count} - \text{negative control}}{\text{positive contol} - \text{negative control}}$$

The percent cytotoxicity for each serially diluted amount of PBMN cells (50:1, 25:1, 12.5:1, and 6.25:1) is plotted against the log of the dilution ratio to generate a cytotoxicity dose response curve. The cytotoxicity dose response curve is used to extrapolate the ratio needed to achieve 10% cytotoxicity. This ratio may be used to calculate a lytic unit using the following formula.

$$\text{lytic unit} = \frac{1000000}{\text{ratio at } 10\% * 4000 * 0.4}$$

In other embodiments, the toxicity dose response curve may be analyzed using a simple linear regression, exponential fit, and/or Von Krogh mathematical models to derive a lytic unit that represents the relative cytotoxicity of the patient's NK cells relative to the SARS-CoV-2 infected target cells.

FIG. 3 is a flowchart depicting a method for measuring the amount of chromium-51 in the sample (e.g., in steps 110, 210) using a gamma counter according to some embodiments. At step 302, aliquots of the supernatant from the SARS-CoV-2 infected target cells treated with serially diluted PBMN cells are transferred to polystyrene tubes. At step 304, the polystyrene tubes are measured using a gamma counter to estimate the amount of chromium-51 in each sample.

FIG. 4 is a flowchart depicting a method for measuring the amount of chromium-51 in the sample (e.g., in steps 110, 210) using a scintillation counter according to some embodiments. At step 402, aliquots of the supernatant from the SARS-CoV-2 infected target cells treated with serially diluted PBMN cells are transferred to respective wells of a 96 well plate. At step 404, liquid scintillation cocktail is added to the respective wells of the 96 well plate. At step 406, the 96 well plate is measured using a scintillation counter estimate the amount of chromium-51 in each sample in each well.

In some embodiments, the susceptibility of the patient to infection by the SARS-CoV-2 virus can be calculated by comparing the lytic unit value of the patient to a plurality of known lytic unit values of a plurality of patients having known susceptibilities to infection by the SARS-CoV-2 virus. While the methods 100, 200, 300, 400 have been described as being performed in various tubes and well plates, these methods may be performed on various microfluidic devices, such as a biochip. In some embodiments, the methods 100, 200, 300, 400 may be automated such that after obtaining the PBMN cells (and optionally the target nasal cells from the patient), the method may be performed without further human intervention.

This method 100 analyzes a patient's PBMN cells (and optionally target nasal cells) to generate a lytic unit, which can be used to extrapolate the cytotoxicity of the patient's NK cells relative to SARS-CoV-2 infected target cells. This data in turn can be used predict the patient's susceptibility to infection by the SARS-CoV-2 virus. Predictions regarding an individual patient's susceptibility to infection by the SARS-CoV-2 virus can inform patient behavior and management of COVID-19 like symptoms. Predictions regarding the susceptibility of a population to infection by the SARS-CoV-2 virus can inform management of a pandemic on a public-health level.

Figure 5:
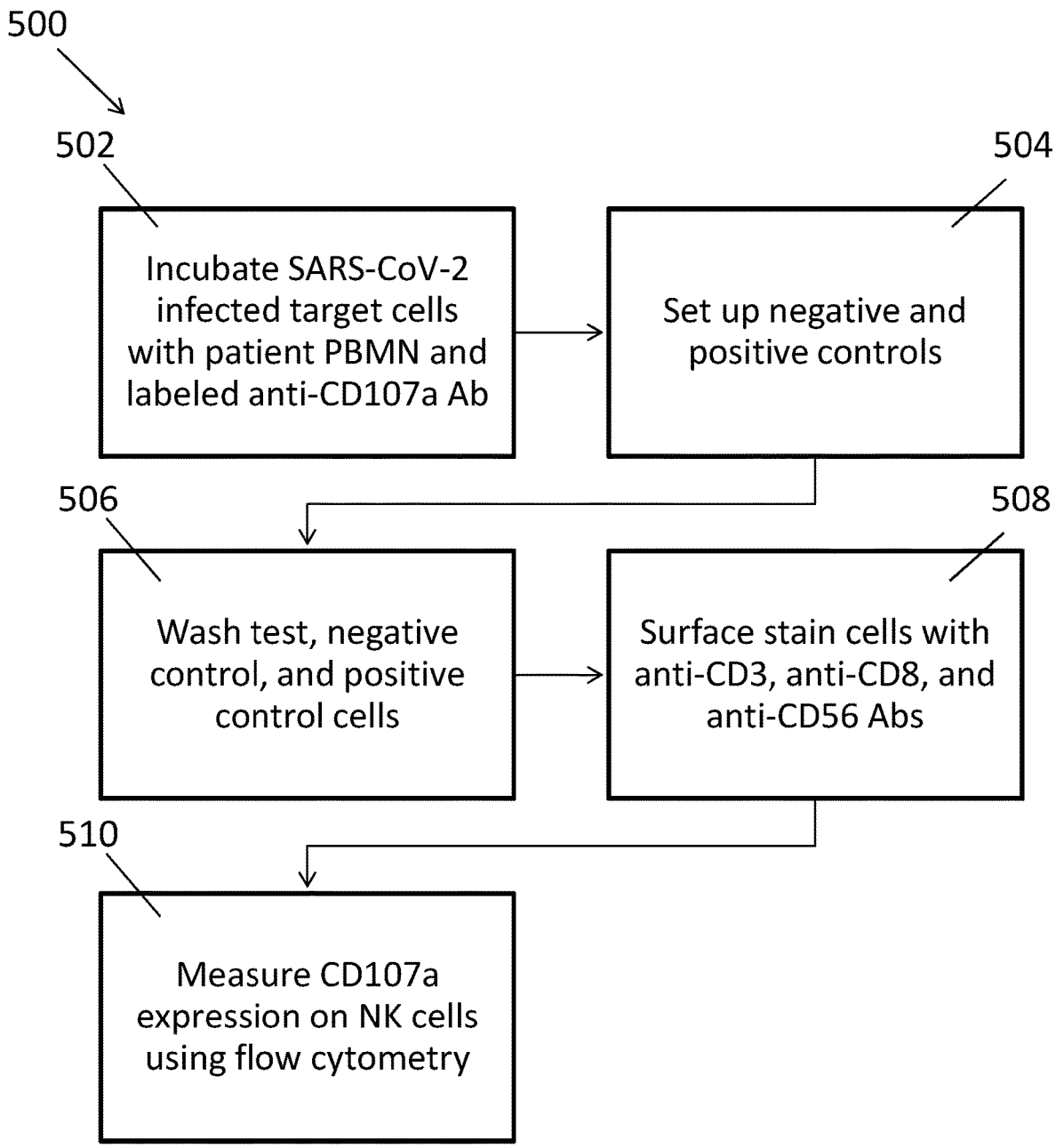
FIG. 5 is a flowchart depicting a method for determining patient susceptibility to infection by the SARS-CoV-2 virus using an NK cell CD107a expression assay according to some embodiments.

Exemplary Method for Determining Susceptibility to SARS-CoV-2 Using NK Degranulation/CD107a Expression Assay As described herein, CD107a is a sensitive marker of NK cell activity including degranulation, which can lead to NK cell mediated apoptosis of target cells. Determining the ability of a patient's NK cells to cause apoptosis of cells infected with SARS-CoV-2 can indicate that patient's susceptibility to infection by SARS-CoV-2. FIG. 5 is a flowchart depicting a method 500 for determining patient susceptibility to infection by the SARS-CoV-2 virus using an NK cell CD107a expression assay according to some embodiments.

At step 502, patient PBMN cells are incubated with SARS-CoV-2 infected target (e.g., human nasal) cells to induce degranulation. At this step, the patient PBMN cells are also incubated with a labeled (e.g., phycoerythrin conjugated) anti-CD107a antibody. In some embodiments, the incubation time is from 4 to 6 hours at 37° C. In some embodiments, monensin is added to the incubation solution to prevent degradation of CD107a/labeled anti-CD107a antibody complexes.

At step 504, negative and positive controls are also established. A negative control may be patient PBMN cells incubated in media and labeled anti-CD107a antibody (optionally secretion inhibitors and CD107a). A positive control may be patient PBMN cells incubated with a superantigen (e.g., staphylococcal enterotoxin B) and labeled anti-CD107a antibody.

At step 506, the incubated PBMN cells (i.e., test=SARS-CoV-2 infected target cells, negative control, and positive control) are washed to remove unbound labeled anti-CD107a antibody.

At step 508, the incubated PBMN cells are stained with anti-CD3, anti-CD8, and anti-CD56 antibodies, each of which is conjugated to a different label (fluorescein isothiocyanate, peridinin chlorophyll protein, and allophycocyanin.

At step 510, the multiply labeled PBMN cells are analyzed using flow cytometry to quantify CD107a expression on NK cells. NK cells are identified (using flow cytometry) as CD3 negative and CD56 positive lymphocytes. In other embodiments, the target and negative and positive control PBMN cells can be treated during leukapheresis to remove T lymphocytes (CD3+) and B lymphocytes (CD19+) to enrich NK cells. In other embodiments, NK cells can be enriched from PBMN cells using fluorescent-activated cell sorting ("FACS") or magnetic-activated cell sorting using antibodies directed to CD16).

This method 500 quantifies CD107a expression in response to SARS-CoV-2 infected target cells by a patient's NK cells, which can be used to extrapolate the patient's NK cells activity and degranulation in response to SARS-CoV-2 infected target cells. This data in turn can be used predict the patient's susceptibility to infection by the SARS-CoV-2 virus.

Figure 6:
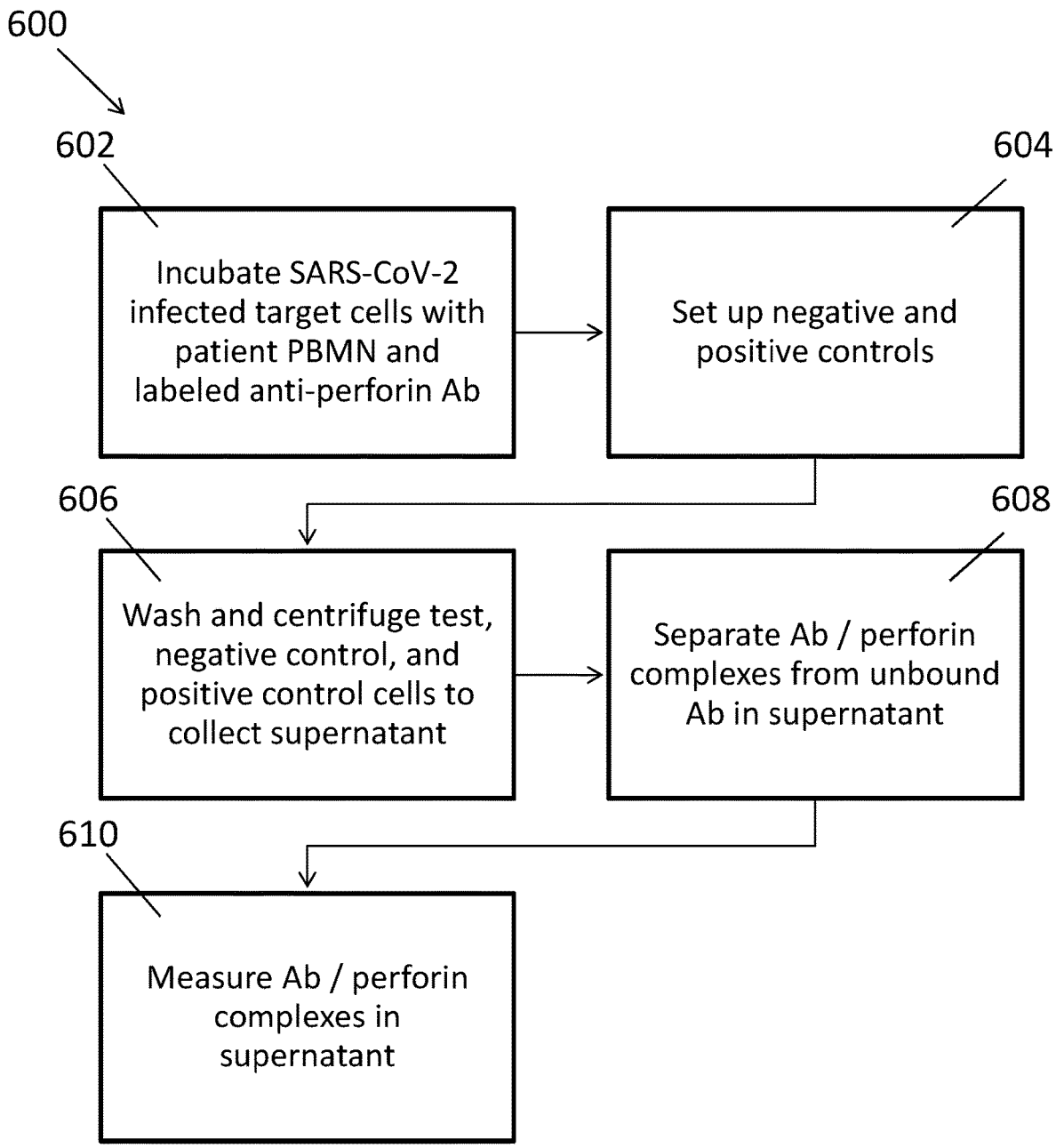
FIG. 6 is a flowchart depicting a method for determining patient susceptibility to infection by the SARS-CoV-2 virus using an NK cell perforin expression assay according to some embodiments.

Exemplary Method for Determining Susceptibility to SARS-CoV-2 Using NK Degranulation/Perforin Expression Assay As described herein, perforin creates openings in the cell membranes of the virally infected cells through which other granzymes enter the virally infected cells and cause apoptosis of the virally infected cells. Determining the ability of a patient's NK cells to cause apoptosis of cells infected with SARS-CoV-2 can indicate that patient's susceptibility to infection by SARS-CoV-2. FIG. 6 is a flowchart depicting a method 600 for determining patient susceptibility to infection by the SARS-CoV-2 virus using an NK cell perforin expression assay according to some embodiments.

At step 602, patient PBMN cells are incubated with SARS-CoV-2 infected target (e.g., human nasal) cells to induce degranulation. At this step, the patient PBMN cells are also incubated with a labeled (e.g., phycoerythrin conjugated) anti-perforin antibody. In some embodiments, the incubation time is from 4 to 6 hours at 37° C. In some embodiments, monensin is added to the incubation solution to prevent degradation of perforin/labeled anti-perforin antibody complexes.

At step 604, negative and positive controls are also established. A negative control may be patient PBMN cells incubated in media and labeled anti-perforin antibody (optionally secretion inhibitors and perforin). A positive control may be patient PBMN cells incubated with a superantigen (e.g., staphylococcal enterotoxin B) and labeled anti-perforin antibody.

At step 606, the incubated PBMN cells (i.e., test=SARS-CoV-2 infected target cells, negative control, and positive control) are washed and centrifuged to collect perforin/labeled anti-perforin antibody complexes in the supernatant.

At step 608, unbound labeled anti-perforin antibody in the supernatant is separated from the perforin/labeled anti-perforin antibody complexes. Various methods to separate the unbound labeled anti-perforin antibody from the perforin/labeled anti-perforin antibody complexes include but are not limited to photo-spectrometry, mass-spectrometry, and electrophoresis.

At step 610, the amount of perforin/labeled anti-perforin antibody complexes in the supernatant is measured (e.g., using fluorescence spectrometry, mass cytometry, and/or flow cytometry). The measured amount of perforin/labeled anti-perforin antibody complexes can be used to estimate perforin expression by the NK cells in response to exposure to SARS-CoV-2 infected target cells.

This method 600 quantifies perforin expression in response to SARS-CoV-2 infected target cells by a patient's NK cells, which can be used to extrapolate the patient's NK cells activity and degranulation in response to SARS-CoV-2 infected target cells. This data in turn can be used predict the patient's susceptibility to infection by the SARS-CoV-2 virus.

Figure 7:
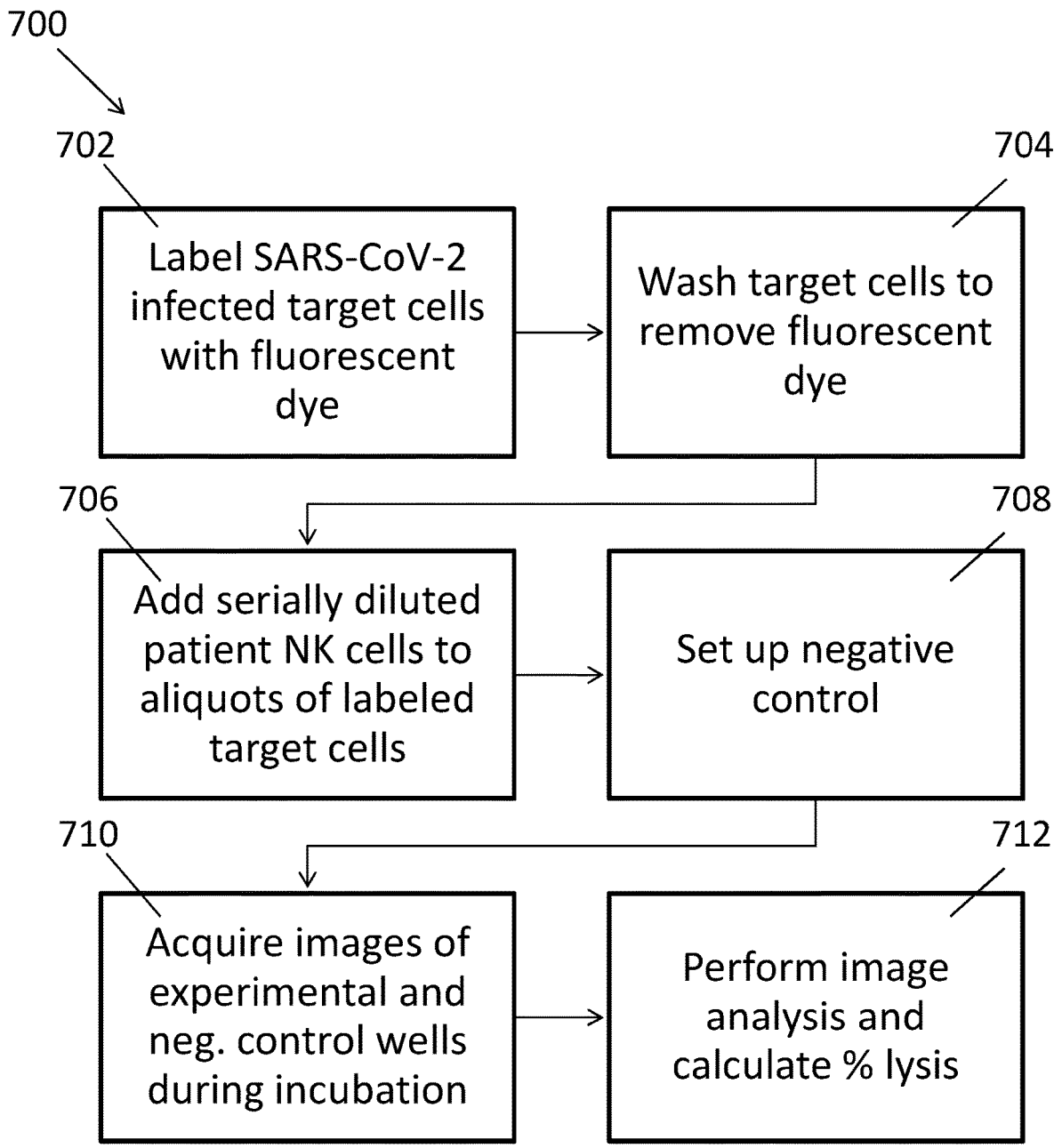
FIG. 7 is a flowchart depicting a method for determining patient susceptibility to infection by the SARS-CoV-2 virus using real-time digital bio-imaging and image analysis according to some embodiments.

Exemplary Method for Determining Susceptibility to SARS-CoV-2 Using Real-Time Digital Bio-Imaging In the method depicted in FIG. 7, a method 700 measures patient NK cell mediated apoptosis of SARS-CoV-2 infected target cells utilizing real-time digital bio-imaging and image analysis software. Such a method 700 determines patient susceptibility to SARS-CoV-2 without using radioactive markers.

FIG. 7 is a flowchart depicting a method 700 for determining patient susceptibility to infection by the SARS-CoV-2 virus by optically measuring patient NK cell mediated apoptosis of SARS-CoV-2 infected target cells according to some embodiments.

At step 702, target cells (e.g., human nasal cells) infected with the SARS-CoV-2 virus are labeled/incubated with a fluorescent dye (e.g., Calcein-AM). Calcein-AM will enter the target cells during incubation, where they will be converted to a green-fluorescent calcein by intracellular esterases.

At step 704, the labeled target cells are washed to remove the extracellular Calcein-AM. In some embodiments, the labeled target cells are washed twice.

At step 706, PBMN cells are collected from the patient (e.g., using density gradient centrifugation) and NK cells are isolated from the patient's PBMN. Then, the NK cells are serially diluted at ("effector: target") ratios of 10:1, 5:1, and 2.5:1. Each of these serially diluted amounts of PBMN cells are incubated with the labeled target cells (e.g., $2 \times 10^4$ cells) in a 96 well plate.

At step 708, negative controls are generated by incubating the labeled target cells with increasing numbers of unlabeled target cells.

At step 710, a cell imaging plate reader is used to acquire images of the wells containing the serially diluted NK cells and the negative controls during incubation. In some embodiments, images are acquired every 10-15 minutes over the course of 4 hours.

At step 712, the % lysis is calculated by performing image analysis (e.g., cell counting) on the acquired images of each experimental and negative control well. The % lysis for each experimental well at each time (t) is calculated using the number of cells detected in each well and the following formula.

$$\% \text{ lysis} = 1 - \frac{exp. \text{ well at } t - exp. \text{ well at } t_0}{neg. \text{ control at } t - neg. \text{ control at } t_0}$$

The % lysis for each serially diluted amount of NK cells (10:1, 5:1, and 2.5:1) is plotted against the log of the dilution ratio to generate a cytotoxicity dose response curve. The cytotoxicity dose response curve can be used to estimate other patients' NK cell mediated apoptosis of SARS-CoV-2 infected target cells. In other embodiments, the toxicity dose response curve may be analyzed using a simple linear regression, exponential fit, and/or Von Krogh mathematical models to estimate the relative cytotoxicity of the patient's NK cells relative to the SARS-CoV-2 infected target cells.

Other Embodiments

In some embodiments, methods detect SARS-CoV-2 spike, M, and N protein specific CD4+ and CD8+ T cells in a recovered/vaccinated patient's PMNC using standard immunological techniques (e.g., detection of co-expression of CD40L and 4-1BB after in vitro stimulation) to estimate susceptibility/immunity to reinfection by SARS-CoV-2.

In some embodiments, methods detect SARS-CoV-2 spike, M, and N protein specific CD4+ and CD8+ T cells in a non-exposed/non-vaccinated patient's PMNC using standard immunological techniques (e.g., detection of co-expression of CD40L and 4-1BB after in vitro stimulation) to estimate susceptibility to infection by SARS-CoV-2 based on cross-reactivity with antigens from other coronaviruses ("common cold coronaviruses"). Estimating susceptibility to infection by SARS-CoV-2 based on cross-reactivity with antigens from common cold coronaviruses also predicts vaccine outcomes.

In some embodiments, methods detect SARS-CoV-2 spike, M, and N protein specific T follicular helper cells in a recovered/vaccinated patient's PMNC using standard immunological techniques (e.g., Activation Induced Marker technique) to estimate susceptibility/immunity to reinfection by SARS-CoV-2.

In some embodiments, methods detect SARS-CoV-2 spike, M, and N protein specific T follicular helper cells in a non-exposed/non-vaccinated patient's PMNC using standard immunological techniques (e.g., Activation Induced Marker technique) to estimate susceptibility to infection by SARS-CoV-2 based on cross-reactivity with antigens from other coronaviruses ("common cold coronaviruses"). Estimating susceptibility to infection by SARS-CoV-2 based on cross-reactivity with antigens from common cold coronaviruses also predicts vaccine outcomes.

The methods (e.g., 100, 200, 500, 600, 700) described herein estimate the susceptibility of a patient's susceptibility to infection by the SARS-CoV-2 virus before such infection. As described herein, determining a patient's susceptibility to infection can provide more flexibility for mitigation of the worldwide COVID-19 infection. For instance, low susceptibility/low morbidity individuals can return to the workforce while individuals with high susceptibility/high morbidity can take more protective measures (e.g., isolation) to avoid infection.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject diagnostic or interventional procedures may be provided in packaged combination for use in executing such interventions. These supply "kits" may further include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

What is claimed is:

1. A method for determining a measure of the cytotoxicity of a patient's cytotoxic immune cells that cause apoptosis of cells infected by SARS-CoV-2 virus, the method comprising:

obtaining a tissue sample from the patient;

obtaining first cytotoxic immune cells from the tissue sample;

obtaining second cells;

infecting the second cells with the SARS-CoV-2 virus;

adding the first cytotoxic immune cells to the second cells;

measuring a property of the second cells related to death of the second cells after adding the first cytotoxic immune cells to the second cells, wherein the property of the second cells comprises a level of radioactivity or a level of fluorescence; and calculating the measure of the cytotoxicity of the first cytotoxic immune cells using at least the property of the second cells.

2. The method of claim 1, wherein the tissue sample is blood from the patient.

3. The method of claim 1, wherein the first cytotoxic immune cells are peripheral blood mononuclear cells of the patient.

4. The method of claim 1, wherein the first cytotoxic immune cells are NK cells of the patient.

5. The method of claim 1, further comprising obtaining the first cytotoxic immune cells using fluorescent-activated cell sorting or magnetic-activated cell sorting.

6. The method of claim 1, further comprising obtaining the first cytotoxic immune cells by removing other cells from the tissue sample using leukapheresis.

7. The method of claim 1, wherein the second cells are cells of the patient.

8. The method of claim 7, wherein the measure of the cytotoxicity of a patient's cytotoxic immune cells has a relationship to a patient's susceptibility to SARS-CoV-2.

9. The method of claim 7, wherein the second cells are at least one of epithelial cells from the patient, mucosal cells from the patient, nasal cells from the patient, or cells of a cell line not related to the patient.

10. The method of claim 1, wherein the property of the second cells is a level of radioactivity or a level of fluorescence in the second cells.

11. The method of claim 1, wherein the property of the second cells is a level of radioactivity, the method further comprising measuring the level of radioactivity in the second cells using a gamma counter or a scintillation counter.

12. The method of claim 1, further comprising calculating a percent cytotoxicity using at least the property of the second cells.

13. The method of claim 12, further comprising calculating a lytic unit value by the following method:
serially diluting the first cytotoxic immune cells in a dilution ratio;
incubating each of the serially diluted first cytotoxic immune cells with a portion of the second cells;
generating a negative control;
generating a positive control;
measuring the level of radioactivity, the level of fluorescence, or the level of surface CD107a expression in each of the serially diluted first cytotoxic immune cells incubated with the portion of the second cells;
calculating a percent cytotoxicity based on measuring the level of radioactivity, the level of fluorescence, or the level of surface CD107a expression;
plotting the percent cytotoxicity against the log of the dilution ratio to generate a cytotoxicity dose response curve;
using the cytotoxicity dose response curve to extrapolate the ratio needed to achieve 10% cytotoxicity; and
using the ratio needed to achieve 10% cytotoxicity; and
calculating a lytic unit using the following formula:

$$\text{lytic unit} = \frac{1,000,000}{\text{ratio at } 10\% \times 4,000 \times 0.4}.$$

14. The method of claim 13, further comprising:
determining a plurality of lytic unit values of a plurality of patients having known measurements of cytotoxicity of the first cytotoxic immune cell; and
comparing the lytic unit value of the patient to said plurality of lytic unit values.

15. The method of claim 1, further comprising growing the second cells in a first solution including a factor related to the property before adding the first cytotoxic immune cells to the second cells,
wherein the factor comprises a radio-labeled marker or a fluorescent marker.

16. The method of claim 1, wherein the method is performed at least partially using a microfluidic device or a biochip.

17. A method for determining a measure of the cytotoxicity of a patient's cytotoxic immune cells that cause apoptosis of cells infected by SARS-CoV-2 virus, the method comprising:
obtaining a tissue sample from the patient;
obtaining first cytotoxic immune cells from the tissue sample;
infecting second cells with the SARS-CoV-2 virus;
adding the first cytotoxic immune cells to the second cells infected with the SARS-CoV-2 virus;
measuring a property of the first cytotoxic immune cells after adding the first cytotoxic immune cells to the second cells, wherein the property comprises the level of surface antigen expression; and
calculating a measure of the cytotoxicity of the first cytotoxic immune cells using at least the property of the first cytotoxic immune cells, wherein the measure of the cytotoxicity of a patient's cytotoxic immune cells has a relationship to a patient's susceptibility to SARS-CoV-2 virus.

18. The method of claim 17, further comprising:
adding an antibody directed to an antigen related to the property of the first cytotoxic immune cells to the second cells infected with the SARS-CoV-2 virus along with the first cytotoxic immune cell; and
incubating the antibody, the first cytotoxic immune cells, and the second cells before measuring the property of the first cytotoxic immune cells.

19. The method of claim 18, further comprising:
preparing a negative control by incubating a first aliquot of first cytotoxic immune cells with the antibody in media; and
preparing a positive control by incubating a second aliquot of first cells with a superantigen and the antibody in media.

20. The method of claim 18, wherein the antigen is CD107a, and wherein the property of the first cytotoxic immune cells is a level of surface CD107a expression.

* * * * *